(12) United States Patent
Duquet et al.

(10) Patent No.: US 9,694,199 B2
(45) Date of Patent: Jul. 4, 2017

(54) FLUID DISPENSER

(71) Applicant: APTAR FRANCE S.A.S., Neubourg (FR)

(72) Inventors: Frederic Duquet, Crespieres (FR); Sandra Martins-Reis, Meudon (FR); Francis Moreau, Sotteville les Rouen (FR); Florence Roullet, Enghien les Bains (FR)

(73) Assignee: APTAR FRANCE S.A.S., Le Neubourg (FR)

( * ) Notice: Subject to any disclaimer, the term of this patent is extended or adjusted under 35 U.S.C. 154(b) by 0 days.

(21) Appl. No.: 14/295,415

(22) Filed: Jun. 4, 2014

(65) Prior Publication Data

US 2014/0296772 A1    Oct. 2, 2014

Related U.S. Application Data

(63) Continuation of application No. 13/767,461, filed on Feb. 14, 2013, now Pat. No. 8,818,500.
(Continued)

(30) Foreign Application Priority Data

Feb. 17, 2012   (FR) ...................................... 12 51482

(51) Int. Cl.
*A61N 5/06*         (2006.01)
*A45D 34/04*        (2006.01)
(Continued)

(52) U.S. Cl.
CPC ........... *A61N 5/0616* (2013.01); *A45D 34/04* (2013.01); *A61M 35/00* (2013.01); *A61N 5/062* (2013.01);
(Continued)

(58) Field of Classification Search
CPC .......... A61N 2005/0644; A61N 5/0616; A61N 2005/0652; A61N 2005/0659;
(Continued)

(56) References Cited

U.S. PATENT DOCUMENTS 3,728,035 A * 4/1973 Reitknecht ......... A46B 11/0079
                                                     401/175
5,292,346 A *  3/1994 Ceravolo ........................ 607/80
(Continued)

FOREIGN PATENT DOCUMENTS

EP       0 743 029 A2   11/1996
WO         00 62701 A2   10/2000
WO   WO 2005095003 A1 * 10/2005 ............. B05B 11/00

*Primary Examiner* — Scott Medway
(74) *Attorney, Agent, or Firm* — Sughrue Mion, PLLC

(57) ABSTRACT

A fluid dispenser including a body (6) receiving a dispenser member (3) connected to a reservoir (1) and to a fluid dispenser orifice (73), an actuator member (4) for actuating the dispenser member (3) and a module (5) comprising at least one source of radiation (51), such as a LED, the body (6) having a module housing (65) wherein the module (5) is received. The dispenser also includes a dispenser and diffuser head (7) mounted on the body (6) and forming an application wall (74) into which the fluid dispenser orifice (73) opens out for applying the fluid coming from the dispenser orifice (73) onto the skin. The module (5) is integral with the dispenser and diffuser head (7), thus forming together an integral unit (U) which is received on and within the body (6).

19 Claims, 3 Drawing Sheets

Related U.S. Application Data

(60) Provisional application No. 61/613,632, filed on Mar. 21, 2012.

(51) Int. Cl.
 *A61M 35/00* (2006.01)
 *B05B 11/00* (2006.01)
 *A61B 90/00* (2016.01)

(52) U.S. Cl.
 CPC .. *A45D 2200/055* (2013.01); *A45D 2200/056* (2013.01); *A45D 2200/205* (2013.01); *A61B 2090/065* (2016.02); *A61N 2005/063* (2013.01); *A61N 2005/0626* (2013.01); *A61N 2005/0644* (2013.01); *A61N 2005/0651* (2013.01); *A61N 2005/0652* (2013.01); *A61N 2005/0662* (2013.01); *A61N 2005/0663* (2013.01); *A61N 2005/0668* (2013.01); *B05B 11/0037* (2013.01); *B05B 11/0048* (2013.01); *B05B 11/3032* (2013.01)

(58) Field of Classification Search
 CPC .... A61N 2005/0651; A61N 2005/0662; A61N 2005/0668; A61N 1/00; A61N 2005/067; A61B 18/203; A61B 2018/00452; A61B 2017/00057; A61B 2017/00734; A61B 2018/0047; A61H 15/0085; A61H 15/02; A61H 2201/0207; A61H 2201/10; A61H 2201/105; A61M 35/003; A46B 2200/1066
 USPC ............. 600/310; 606/2, 20; 607/96; 604/20
 See application file for complete search history.

(56) References Cited

U.S. PATENT DOCUMENTS

| | | | |
|---|---|---|---|
| 5,820,626 A | 10/1998 | Baumgardner | |
| 6,021,960 A * | 2/2000 | Kehat | 239/289 |
| 6,126,290 A * | 10/2000 | Veigel | 362/96 |
| 6,623,272 B2 * | 9/2003 | Clemans | 433/215 |
| 6,743,222 B2 | 6/2004 | Durkin et al. | |
| 6,911,010 B2 | 6/2005 | Dirks et al. | |
| 7,178,746 B2 * | 2/2007 | Gross | 239/552 |
| 7,291,140 B2 | 11/2007 | MacFarland et al. | |
| 7,384,405 B2 | 6/2008 | Rhoades | |
| 7,758,525 B2 | 7/2010 | Thiebaut et al. | |
| 7,950,396 B2 | 5/2011 | Rose et al. | |
| 8,523,791 B2 | 9/2013 | Castel | |
| 8,602,774 B2 * | 12/2013 | Wasylucha | 433/89 |
| 2002/0183724 A1 * | 12/2002 | Neev | 606/2 |
| 2004/0147984 A1 | 7/2004 | Altshuler et al. | |
| 2006/0195023 A1 * | 8/2006 | Acosta et al. | 600/316 |
| 2006/0289679 A1 * | 12/2006 | Johnson | B05B 1/3046 239/333 |
| 2007/0060984 A1 | 3/2007 | Webb et al. | |
| 2007/0185553 A1 | 8/2007 | Kennedy | |
| 2007/0198004 A1 | 8/2007 | Altshuler et al. | |
| 2008/0014011 A1 * | 1/2008 | Rossen | 401/195 |
| 2008/0091179 A1 * | 4/2008 | Durkin et al. | 606/9 |
| 2009/0194474 A1 * | 8/2009 | Tranchant et al. | 210/251 |
| 2009/0306577 A1 * | 12/2009 | Akridge et al. | 604/20 |
| 2010/0063565 A1 * | 3/2010 | Beerwerth et al. | 607/88 |
| 2011/0123958 A1 | 5/2011 | Piergallini et al. | |
| 2012/0109041 A1 * | 5/2012 | Munz | 604/20 |
| 2013/0032610 A1 * | 2/2013 | Muller | 222/113 |

* cited by examiner

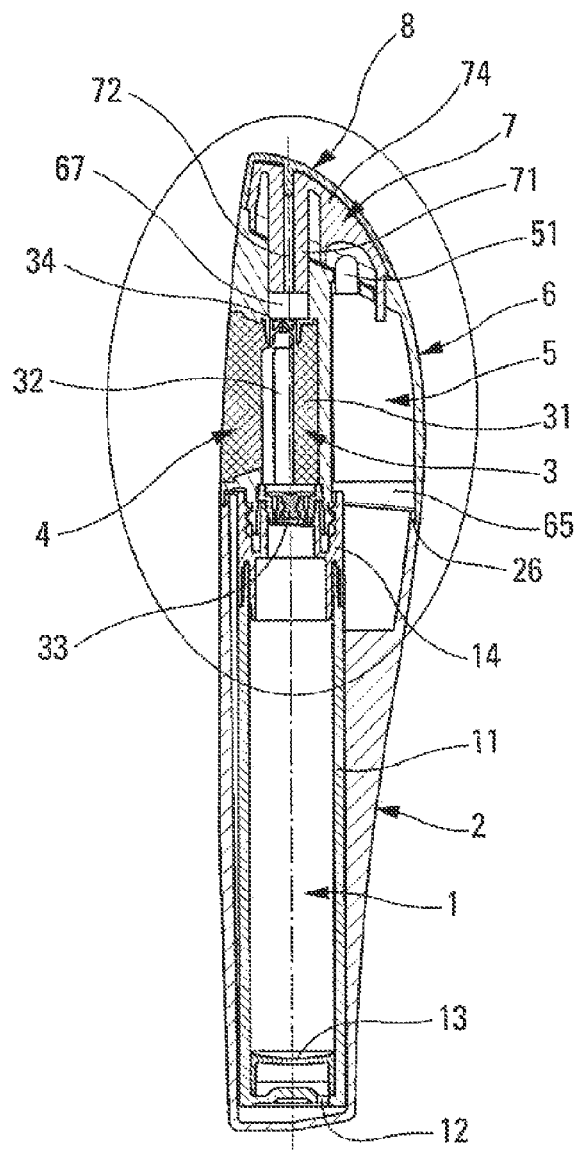
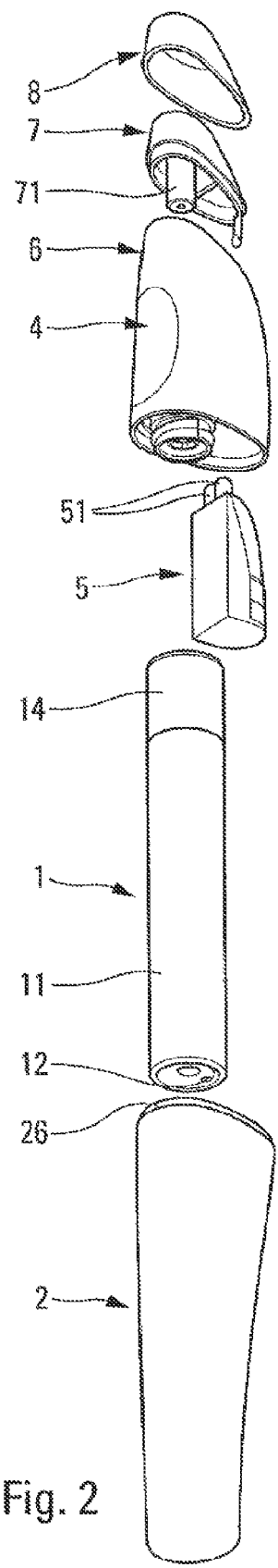
Fig. 1
Fig. 2

FLUID DISPENSER

CROSS REFERENCE TO RELATED APPLICATION

This application is a Continuation application of U.S. application Ser. No. 13/767,461, filed on Feb. 14, 2013, which claims the benefit under 35 U.S.C. §119(e) of U.S. provisional patent application Ser. No. 61/613,632, filed Mar. 21, 2012, and priority under 35 U.S.C. §119(a)-(d) of French patent application No. FR 12 51482, filed Feb. 17, 2012; the entire disclosures of the prior applications are considered part of the disclosure of the accompanying Continuation application, and are hereby incorporated by reference.

TECHNICAL FIELD

The present invention relates to a fluid dispenser comprising: a fluid reservoir; a fluid dispenser member that is connected to the reservoir; an actuator member for actuating the dispenser member; a fluid dispenser orifice that is connected to the dispenser member; and an application wall for applying the fluid coming from the dispenser orifice onto the skin. This dispenser, which can also be described as an applicator, finds an advantageous application in the fields of cosmetics and pharmacy, and more generally in the field of treating and caring for the skin.

BACKGROUND OF THE INVENTION

In the prior art, numerous dispensers already exist that are capable of dispensing fluid, optionally in metered manner, for application to an application surface, such as the skin, the nails, the mucous membranes, the hair, etc. In general, the dispenser member is a pump or a valve that may be actuated by means of a pusher on which pressure is exerted by means of one or more fingers. The fluid from a reservoir is put under pressure in the pump chamber or valve before being forced through a dispenser orifice that is usually arranged in an application wall for coming into contact with the skin. The application wall is used to spread the dispensed fluid over a greater or smaller area of the skin.

Naturally, the effectiveness of this skin treatment depends mainly on the characteristics of the fluid that is applied, and on the quality of its application. It also depends on the type and quality of the skin. An object of the present invention is to increase the effectiveness of the skin treatment by preparing the skin before applying the fluid. Another object is to treat the skin while applying the fluid, and even after applying the fluid.

BRIEF SUMMARY OF THE INVENTION

To do this, the present invention proposes that the dispenser further comprises at least one source of radiation, such as a light-emitting diode (LED), emitting monochromatic light in the spectrum lying in the range 400 nanometers (nm) to 700 nm, and having an anti-inflammatory action and/or a stimulating action for stimulating skin-regeneration metabolisms.

This type of light is already used in institutes for combating inflammation, boosting collagen synthesis, improving vascularization, accelerating the repair of stretch marks or scar tissue, and also for reducing pain. Thus, it is already known to subject the skin to radiation that is pure in color or "monochromatic", in the range blue to red. However, it is especially the red and the near infrared that provide such performance. Infrared light is thermal radiation at a wavelength of about 700 nm or longer. The light heats the area being treated, stimulates blood circulation, heats tissues, and activates fibroblasts. With regard to red light, it mainly stimulates metabolisms for regenerating the skin by producing new collagen: this is referred to as collagen neosynthesis. In order to generate such light, it is possible to use LEDs or low power lasers in low level laser therapy (LLT).

The present invention specifically makes provision for associating or combining a conventional dispenser/applicator with one or more sources of radiation of this type for the purpose of treating the skin before, during, and/or after applying the fluid. The effectiveness of the fluid is thus optimized by acting on the quality of the skin. US2007/185553 and US2007/198004 describe such devices for a therapeutic purpose. The ergonomics and shape of the devices are not adapted to an individual utilization for cosmetics application.

In order to overcome the problems of the prior art devices, the present invention proposes a fluid dispenser comprising:
a fluid reservoir; and
a body receiving:
  a fluid dispenser member that is connected to the reservoir;
  an actuator member for actuating the dispenser member;
  a dispenser and diffuser head forming a fluid dispenser orifice that is connected to the dispenser member, and an application wall for applying the fluid coming from the dispenser orifice onto the skin;
  a module comprising at least one source of radiation, such as an LED, each emitting monochromatic light in the spectrum lying in the range 400 nm to 700 nm, and having an anti-inflammatory action and/or a stimulating action for stimulating skin-regeneration metabolisms;
the dispenser and diffuser head comprising a source housing, and in that the body comprises a module housing wherein the module is received, this module housing communicating with the source housing so that the source of radiation extends in the source housing of the head.

Thus, the dispenser has a compact shape. Advantageously, the module is received in a removable manner within the module housing. According to a practical embodiment, the module is integral with the dispenser and diffuser head, thus forming together an integral unit which is received in a removable manner on and within the body. According to another feature, the body has a horizontal cross-section of oblong shape where the dispenser member, the actuator member and the module housing with the module are arranged, the dispenser member being advantageously arranged between the actuator member and the module housing, the actuator member being arranged at a part of greatest curvature of the body. Preferably, the dispenser presents the general shape of a pen, with the body arranged between the dispenser and diffuser head and the reservoir.

The dispenser of the invention mat thus be easily handled as a pen by a user for a personal application, namely at the face.

Advantageously, the source of radiation may emit red light at about 660 nm.

According to another advantageous characteristic, the source of radiation may emit light from the application wall. Preferably, the source of radiation emits light through the application wall.

Advantageously, at least locally, the application wall is made out of a material that is transparent and/or translucent to the light emitted by the source of radiation, the source emitting light through said material towards the skin. Preferably, the application wall guides or conveys the light emitted by the source of radiation. Thus, the application wall performs two functions, namely a first function of transmitting/guiding the light coming from the source of radiation, and a more conventional second function of applying/spreading the dispensed fluid. The fact of using the application wall to guide or convey the light is a characteristic that is particularly advantageous. Another advantage that is inherent to this embodiment resides in the fact that the distance between the light source and the skin is constant and unvarying, since it is determined by the application wall that is itself at a determined and unvarying distance relative to the light source. It is thus possible to determine, with accuracy, the length of time during which the skin is irradiated or illuminated, as a function of the power of the emitted light, of the distance between the light source and the application wall, and of the diffusing qualities and characteristics of the application wall. Thus, it suffices for the user to be exposed to the light only once in order to guarantee the desired effect. In addition, because the light is emitted through the application wall, this necessarily implies that the fluid is separated from the light source by the application wall, such that the light source cannot be soiled with fluid in any way.

In another advantageous aspect of the invention, the dispenser orifice opens out to the application wall with a direction that is substantially parallel to the direction of the light emitted by the source of radiation. This implies that the fluid may be dispensed and applied to the skin directly after the exposure-to-light stage, without manipulating the dispenser other than by pressing on the actuator member. In other words, the exposure-to-light and the fluid dispensing/application stages may take place while the dispenser is being held in a single and determined orientation.

According to another particularly advantageous characteristic of the present invention, the dispenser further includes power supply means for powering the source of radiation, which means are activated only when the application wall is in contact with the skin Advantageously, the application wall causes a switch to operate so as to trigger the activation of the power supply means for powering the source of radiation. This means that the light is emitted only when the skin is at a distance that is predetermined by the distance between the application wall and the source of radiation. As a result, it is impossible to irradiate, deliberately or accidentally, sensitive organs such as the eyes. Applying the application wall to an eye is unlikely. It is possible to use any known prior-art technique for using the application wall as a switch for triggering the activation of the power supply for powering the source of radiation. By way of example, provision may be made to move the application wall a little, like a mechanical switch. The application wall may also be used as a contact element that is sensitive to heat, touch, presence, etc.

In a practical embodiment, the application wall is formed by a dispenser and transmitter head that includes a source housing for receiving the source of radiation. Thus, the source of radiation is completely protected in its housing. It cannot be damaged or contaminated.

In another advantageous aspect of the invention, the actuator member is movable in an actuation direction that is substantially perpendicular to a direction for dispensing the fluid through the dispenser orifice. Thus, the dispenser may be taken hold of and used like a pen, pressing laterally on the actuator member by means of the index finger, which makes it possible to hold the dispenser with great accuracy.

In another practical aspect of the invention, the source of radiation forms part of a module that further includes electronic circuitry, power supply means, activator means for activating the power supply means, and a timer. The activator means that trigger the power supply means may include a sensor that is sensitive to pressure, contact, presence, or heat, or they may even be in the form of an electric contactor.

In a practical embodiment, the reservoir is in the form of a removable and replaceable cartridge that is arranged in a casing that is connected, in removable manner, to a body that receives the dispenser member, the actuator member, and a dispenser head that forms the dispenser orifice, the application wall, and a source housing receiving the source of radiation. The dispenser thus comprises two distinct sub-assemblies, namely a lower sub-assembly that is constituted by the reservoir and the casing, and an upper sub-assembly that is constituted by the body, the dispenser member, the actuator member, the dispenser head, the module, and optionally a cap that comes to cover the application wall.

The spirit of the invention resides in the fact of incorporating, in a single dispenser, one or more sources of radiation capable of treating the skin, and an applicator capable of spreading a fluid on the skin. The compact configuration and the ergonomic shape, comparable to a pen, allow an easy utilization.

BRIEF DESCRIPTION OF THE DRAWINGS

The invention is described more fully below with reference to the accompanying drawings, which show an embodiment of the invention by way of non-limiting example.

In the Figures:

FIG. 1 is a vertical section view through a fluid dispenser of the invention;

FIG. 2 is an exploded perspective view of the FIG. 1 dispenser;

DETAILED DESCRIPTION

Figure 3:
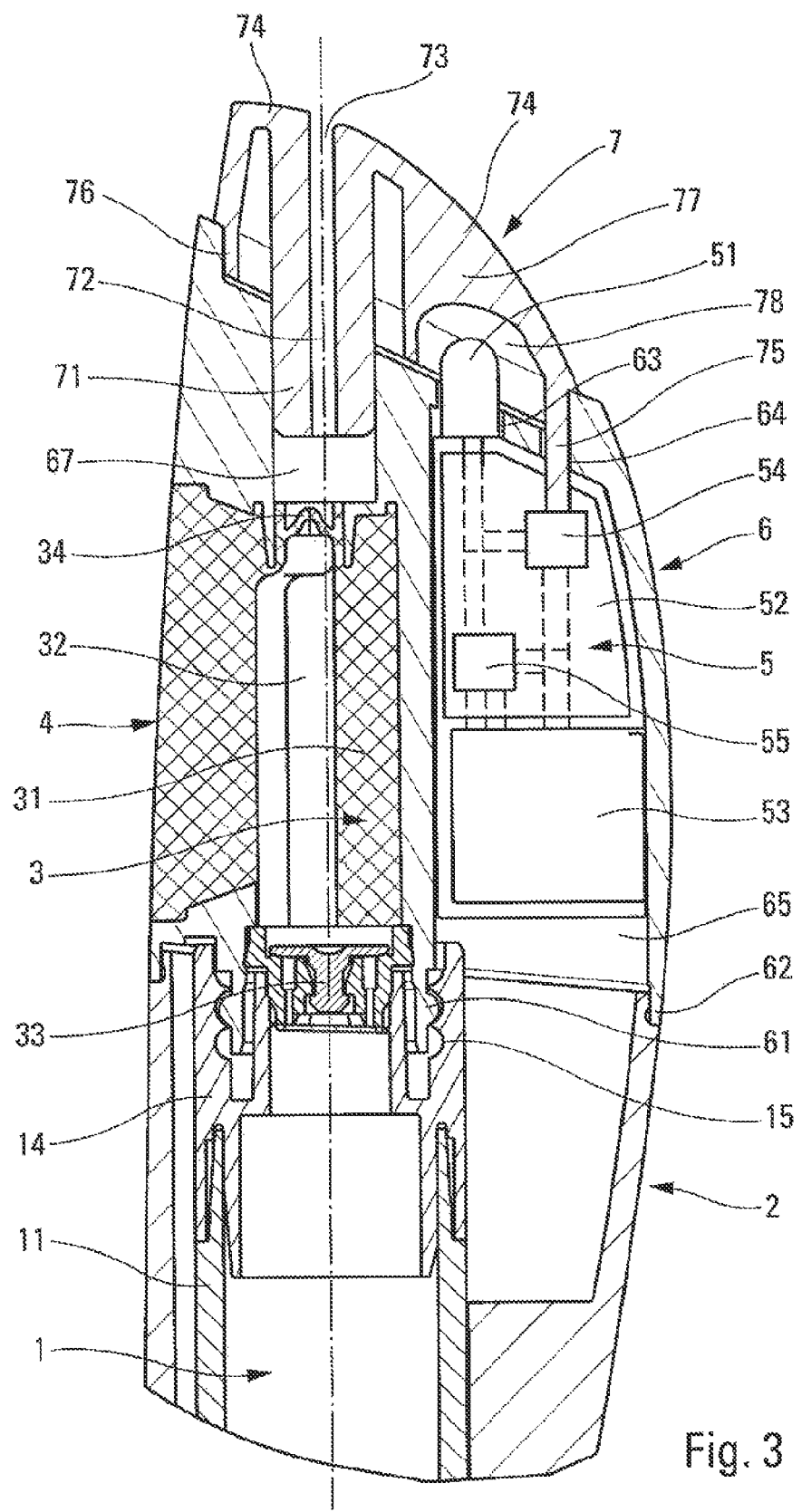
FIG. 3 is a greatly enlarged view of the circled top portion of the FIG. 1 dispenser, showing, in diagrammatic manner, some of the components of the module.

Reference is made to FIGS. 1 to 3 taken together in order to describe in detail the structure and the operation of a dispenser in a non-limiting embodiment of the invention.

The dispenser comprises: a fluid reservoir 1; a casing 2 in which the reservoir 1 is received; a dispenser member 3, specifically a pump; an actuator member 4 for actuating the pump 3, and that is specifically incorporated in the pump; a module 5 that is provided with one (or more) sources of radiation 51; a body 6 that receives the pump 3, the actuator member 4, and the module 5; and finally a dispenser head 7 that is mounted on the body 6. Optionally, the dispenser may also include a protective cap 8 that covers the dispenser head 7. With the exception of the module 5, all of the component elements of the dispenser may be made by injection-molding plastics material. The dispenser is shown approximately life-size in FIG. 1. It should be observed that the dispenser is not circularly symmetrical, but generally convex unilaterally towards the module 5. The dispenser is intended to be taken hold of like a pen, with the convex portion oriented towards the palm of the hand, and the actuator member 4 being intended to come into contact with the index finger. In FIG. 2, it should be observed that the top portion of the casing 2 and the body 6 present a horizontal cross-section of elongate shape that is oblong or egg-shaped. The actuator member 4 is advantageously arranged at a part of greatest curvature of the body 6. The dispenser thus presents a configuration that is narrower in one direction than in the other, thereby making it easier to hold it in the hand like a pen. Intuitively, the user takes hold of the dispenser in such a manner as to position the actuator member 4 under the index finger. The dispenser is held mainly between the thumb and the middle finger at the body 6, on either side of the module 5 and the actuator member 4.

The fluid reservoir 1 may be made with a section that is circularly-cylindrical, constituting a cylinder 11 slidably receiving a follower piston 13. In order to prevent any suction in the cylinder below the follower piston 13, the cylinder is provided with a vent hole 12. At its top end, the cylinder 11 is provided with a fastener ring 14 that is provided with an internal thread 15. In entirely conventional manner, the follower-piston 13 moves inside the cylinder 11 as fluid is extracted therefrom. Thus, air never penetrates inside the reservoir 1. This is a particular and non-limiting embodiment: any other reservoir, with or without air inlet, can be used in the present invention.

The reservoir 1 is arranged inside the casing 2, the main function of which is to protect and mask the reservoir 1. As mentioned above, it should be observed that the casing 2 presents a complex geometrical shape, with a top portion of horizontal cross-section that is oblong or egg-shaped. However, the casing 2 internally defines a housing for axially receiving the reservoir 1. It can thus be said that the casing 2 forms a unilateral projection that extends on one side only of the reservoir 1, as can be seen in FIGS. 1 and 3. The casing 2 includes an opening edge 26 for coming into engagement with the body 6 as described below.

The dispenser member 3, specifically a pump, comprises a pump body 31 that defines a pump chamber 32 that, at its bottom portion, communicates with the reservoir 1 through an inlet valve 33, and that, at its top portion, is provided with an outlet valve 34. The pump 3 is of a particular type, specifically a "diaphragm" pump, given that the actuator member 4 is in the form of a flexible actuator wall that advantageously forms an integral part of the pump body 3. By pressing by means of finger, e.g. the index finger, on the deformable wall 4, the working volume of the pump chamber 32 is reduced, and this puts the fluid that it contains under pressure, closes the inlet valve 33, and opens the outlet valve 34 through which the fluid under pressure is forced. A pump of that type and its operation are known in the field of "diaphragm" pumps. The particular structure of the pump 3 is not critical to the present invention: another type of pump could be used without going beyond the invention.

The pump 3 with its actuator member 4 are incorporated in the body 6 that, by way of example, may be overmolded onto the pump 3 and its actuator member 4. The body 6 forms an assembly bushing 61 that is externally threaded so that the internal thread 15 of the ring 14 may come into engagement therewith, so as to connect the opening of the reservoir 1 to the inlet of the pump where the inlet valve 33 is situated. Another type of assembly, e.g. a snap-fastening or a bayonet fastening, may also be used to connect the reservoir 1 to the body 6, or more generally to the inlet of the pump 3. In the invention, it is preferable for the reservoir 1 to be connected to the body 6 in removable manner, so that it may be replaced like a cartridge. To this end, it should be observed that, at its opening edge 26, the casing 2 is snap-fastened to a flange 62 that is formed at the bottom end of the body 6. In order to replace the reservoir 1 once it is empty, it suffices to separate the casing 2 from the body 6, and to unscrew the reservoir 1 from the threaded bushing 61 of the body 6. By way of example, provision may be made for the opening of the reservoir 1 to be closed initially by a film that is pierced by some member that is secured to the body 6 or to the inlet valve 33, while the reservoir 1 is being screw-fastened on the threaded bushing 61. It is then possible to define two sub-assemblies, namely a lower sub-assembly that is constituted by the reservoir 1 and the casing 2, and an upper sub-assembly that is constituted by the body 6 and all of the component elements that are mounted thereon.

At the outlet of the outlet valve 34, the body 6 forms an outlet chimney 67 that leads to the dispenser orifice 73, as described below. The body 6 also defines a module housing 65 inside which the module 5 is received. The body 6 forms a first slot 63 through which the light source 51 extends, e.g. a source in the form of one or more LEDs. The body 6 defines a second slot 64 having a function that is explained below.

The dispenser and applicator head 7 is an asymmetrical part that may be made by injection-molding a plastics material that is transparent or translucent. The head 7 includes an outlet tube 71 that internally defines an outlet channel 72 that connects the outlet chimney 67 to the dispenser orifice 73. By way of example, the outlet tube 71 may be force-fitted in the chimney 67. The head 7 also includes an application wall 74 into which the dispenser orifice 73 opens out. In the embodiment in the figures, the application wall 74 extends mainly on the righthand side of the dispenser orifice 73, defining a curved slope. It should be observed that the application wall 74 presents extra thickness that serves as a light waveguide 77, as described below. The extra thickness forming a wave guide 77 defines a source housing 78 for receiving the source(s) of radiation 51. The head 7 also includes a peripheral stabilizing lip 76, so as to ensure that the head 7 is held stationary on the body 6 in stable and permanent manner. The head 7 also includes a transmission pin or tab 75 that extends through the second slot 64 so as to be capable of penetrating into the module housing 65. The application wall 74 is made, at least in part or locally, out of a material that is transparent or translucent to visible light and to infrared. By way of example, it is possible to use copolyesters or styrenes to make the application wall, and even the head 7 as a whole.

It should already be understood that it is possible to dispense fluid through the dispenser orifice 73 at the application surface 74 by actuating the actuator member 4 of the dispenser member 3 that makes it possible to take the fluid from the reservoir 1, to put it under pressure in the chamber 32, and to force it through the outlet valve 34, the chimney 67, and the outlet duct 72, until it reaches the dispenser orifice 73. Once the dispensed fluid is present on the application wall 74, the user may apply it and spread it over an application surface, such as the skin. The dispensed fluid is preferably a viscous fluid, such as a cream, a gel, a pomade, etc.

The module 5 is an electronic module that is provided with one or more source(s) of radiation 51 in the form of one or more LEDs, for example. Each LED emits monochromatic light. By way of example, it is possible to provide a blue LED and/or a red LED. The module 5 may be in the form of a small case that has one or two LEDs on top. The module comprises: power supply means 53, e.g. in the form of a battery; electronic circuitry 52, e.g. in the form of a small printed circuit card; activator means 54 for triggering the powering of the source 51 by the power supply means 53; and a timer 55 that determines the length of time that the light source 51 is powered. In other words, the activator means 54 determine the start of the stage during which the light source 51 is powered, and the timer 55 determines the end of that stage. Naturally, the module 5 may also incorporate other electronic components that are capable of performing other functions. The module 5 is arranged and held inside the module housing 65 that is formed by the body 6. In this mounted position, the light source 51 extends through the first slot 63 of the body 6 into a source housing 78 that is defined inside the dispenser head 7. A large portion of the source housing 78 is formed by the application wall 74 that is made out of a material that is transparent or translucent to the light emitted by the source of radiation 51. To this end, the light emitted by the source 51 may be in a spectrum lying in the ultraviolet to infrared range of 400 nm to 700 nm. By way of example, it is possible to use a red light having a wavelength that is about 660 nm. Skin that is exposed to such a light is, amongst other things, subjected to stimulation of its metabolisms regenerating skin, and produces collagen. Thus, the light is emitted into the source housing 78, is guided by the extra thickness forming a waveguide 77, and then exits the application wall 74 so as to reach the skin that is in contact with the application surface 74. Preferably, the transparent or translucent material that constitutes the application wall 74 diffuses in all directions the light that passes therethrough, in such a manner as to make the distribution of light uniform over the surface of the skin. When the head 7 is made entirely out of such a diffusing material, all of the component elements of the head, including the outlet tube 71, may serve as waves to guide and transmit.

In addition, the transmission pin 75 extends from the application surface 74, through the second slot 64, and into the module housing 65, so as to co-operate directly or indirectly with the activator means 54. The transmission pin 75 serves as a conducting or transmitting guide enabling information to be passed from the application wall 74 to the module 5. By way of example, provision may be made for the pin 75 to be capable of transmitting a thrust force to the activator means 54, which thrust force is exerted on the application surface 74. In this configuration, the activator means 54 may comprise a thrust detector, or merely an electric contactor that is sensitive to thrust. When the activator means 54 perceive pressure, they trigger the electric powering of the light source 51. Provision may also be made for the transmission pin 75 to be adapted to transmit heat, contact with another element, or the absence of light. It is also possible to provide other transmission means, such as electrical, thermal, or optical conductors. In these configurations, provision can be made for the activator means 54 to comprise a heat, presence, or absence-of-light sensor. It is also possible to provide an electronic contactor at the application wall 74. In the prior-art, numerous techniques exist for transmitting information to activator means. In the present invention, the object is to activate the light source 51 only when the application wall 74 is in contact with the skin. Such contact with the skin creates pressure, heat transmission, an electric current, and/or darkening of the application wall: one or more or these parameters can be transmitted by means of the transmission pin 75 to the module 5 so that it triggers powering of the light source 51. Any triggering that is accidental or damaging to health is thus avoided. After activation, the source of radiation 51 remains powered for a length of time that is predetermined by the timer 55, which predetermined length of time enables the area of skin to which the fluid is applied to be treated adequately. However, when the wall is no longer in contact with the skin, the power should be switched off, thereby interrupting the timer so as to avoid accidental irradiation. When the applicator is briefly lifted off the skin, provision may also be made for the timing by the timer merely to be suspended and not reinitialized.

It should be observed that the distance between the light source 51 and the skin is determined by the application surface 74 against which the skin comes into contact. It is thus possible to determine, with accuracy, the power of the light source 51, its distance to the application surface 74, and the length of time during which it is activated in order to obtain the desired skin treatment. In addition, given that the light source 51 is arranged under the application wall 74, it need not come into direct contact with the fluid: it thus cannot be soiled by said fluid.

It should also be observed that in the event of failure or malfunctioning, the module 5 can easily be removed from its housing 65 so as to be replaced by a new module. The module 5 is thus merely in the form of a refill. It is also possible to remove the module 5 from its housing 65 merely so as to replace or recharge the power supply means 53.

Given that the application surface 54 can easily be cleaned, it is guaranteed that the skin is exposed in constant and reproducible manner to the light from the source of radiation 51.

Figure 4:
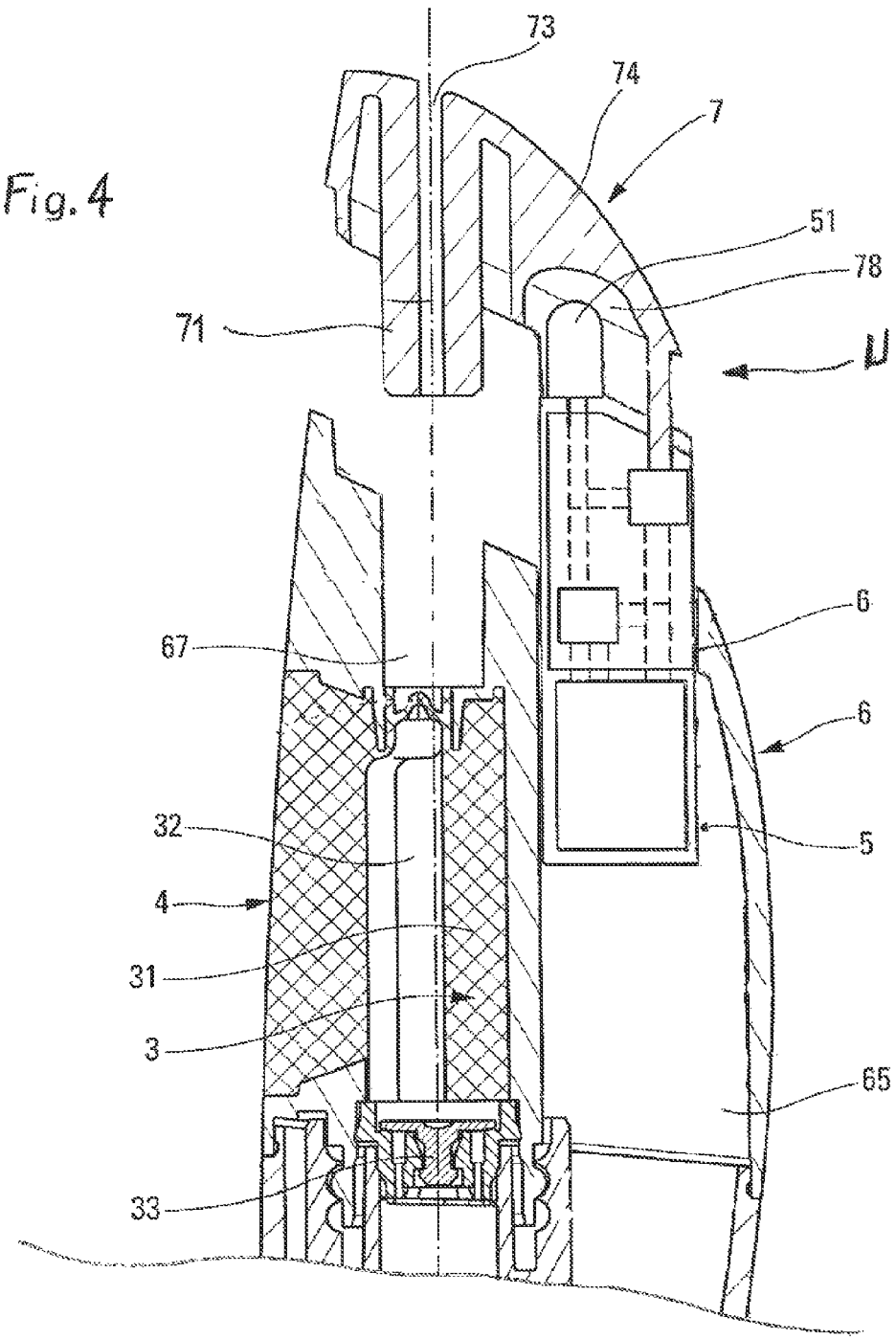
FIG. 4 is a view like FIG. 3 for an alternative embodiment in a disassembled condition.

FIG. 4 represents an alternative embodiment wherein the head 7 and the module 5 form together an integral unit U which is mounted on the body 6. The unit U is represented when being mounted or removed in FIG. 4. The module is already inserted through the unique window 66 which permits access to the module housing 65. The outlet tube 71 is aligned with the outlet chimney 67.

By means of the invention, the effectiveness of a conventional dispenser/applicator is considerably improved by the prior, simultaneous, and/or subsequent treatment of the area of skin by means of appropriate light.

The invention claimed is:

1. A fluid dispenser comprising:
a body receiving:
a fluid dispenser member connected to a fluid reservoir and to a fluid dispenser orifice;
an actuator member for actuating the dispenser member;
a module comprising at least one source of radiation, the module received within a portion of the body that defines a module housing;
a dispenser and diffuser head mounted on the body and forming an application wall into which the fluid dispenser orifice opens out for applying the fluid coming from the dispenser orifice onto the skin,
wherein the module is integral with the dispenser and diffuser head, thus forming a single unit construction,
wherein the body has a horizontal cross-section of oblong shape where the dispenser member, the actuator member and the module housing with the module are arranged, the dispenser member being advantageously arranged between the actuator member and the module housing, the actuator member being arranged at a part of the body having a greatest radius of curvature.

2. The dispenser according to claim 1, further comprising as casing containing the fluid reservoir and wherein the single unit construction is received in a removable manner on the casing.

3. A fluid dispenser comprising:
a body receiving:
- a fluid dispenser member connected to a fluid reservoir and to a fluid dispenser orifice;
- an actuator member for actuating the dispenser member;
- a module comprising at least one source of radiation, the module received within a portion of the body that defines a module housing;
- a dispenser and diffuser head mounted on the body and forming an application wall into which the fluid dispenser orifice opens out for applying the fluid coming from the dispenser orifice onto the skin,
- wherein the module is integral with the dispenser and diffuser head, thus forming a single unit construction,
- wherein a portion of the dispenser and diffuser head defines a source housing, and the module housing communicates with the source housing so that the source of radiation extends into the source housing of the dispenser and diffuser head.

4. The dispenser according to claim 1, presenting the general shape of a pen, with the dispenser and diffuser head arranged at the top of the body.

5. The dispenser according to claim 1, wherein the source of radiation emits red light at about 660 nm.

6. The dispenser according to claim 1, wherein the source of radiation emits light through the application wall, the application wall being made out of a material that is transparent and/or translucent to the light emitted by the source of radiation, the source emitting light through said material towards the skin.

7. The dispenser according to claim 1, wherein the dispenser orifice opens out to the application wall with a direction that is substantially parallel to the direction of the light emitted by the source of radiation.

8. The dispenser according to claim 1, further including power supply means for powering the source of radiation, which means are activated only when the application wall is in contact with the skin.

9. The dispenser according to claim 7, wherein the application wall is configured to deflect to operate a switch so as to trigger the activation of the power supply means for powering the source of radiation.

10. A fluid dispenser comprising:
a body receiving:
- a fluid dispenser member connected to a fluid reservoir and to a fluid dispenser orifice;
- an actuator member for actuating the dispenser member;
- a module comprising at least one source of radiation, the module received within a portion of the body that defines a module housing;
- a dispenser and diffuser head mounted on the body and forming an application wall into which the fluid dispenser orifice opens out for applying the fluid coming from the dispenser orifice onto the skin,
- wherein the module is integral with the dispenser and diffuser head, thus forming a single unit construction,
- wherein the actuator member is movable in an actuation direction that is substantially perpendicular to a direction for dispensing the fluid through the dispenser orifice.

11. The dispenser according to claim 1, wherein the module further includes electronic circuitry, power supply means, activator means for activating the power supply means, and a timer.

12. The dispenser according to claim 1, wherein the reservoir is in the form of a removable and replaceable cartridge that is arranged in a casing that is connected, in removable manner, to the body.

13. The dispenser according to claim 1, wherein the module and the dispenser and diffuser head form the single unit construction configured to permit assembly of the single unit construction with the body by inserting the module of the single unit construction into the module housing while the module remains as the single unit construction with the dispenser and diffuser head, and wherein a projecting portion of the dispenser and diffuser head is within the body.

14. The dispenser according to claim 1, wherein a projecting portion of the dispenser and diffuser head defines a conduit that fluidly couples with the fluid dispenser member within the body.

15. The dispenser according to claim 1,
wherein the dispenser and diffuser head comprises a flange portion,
wherein a projecting portion is formed within the flange portion, and
wherein both the dispenser and diffuser head and the projecting portion are coupled to body.

16. The dispenser according to claim 15, wherein the flange matches a profile of a distal end of the body.

17. The dispenser according to claim 1, wherein the dispenser and diffuser head comprises a transmission pin that penetrates into the module, the transmission pin being configured to serve as a conducting or transmitting guide.

18. The dispenser according to claim 1,
wherein, the dispenser and diffuser head comprises a projecting portion, and
wherein the projecting portion of the dispenser and diffuser head is within the body.

19. The dispenser according to claim 1, wherein the module, the dispenser and diffuser head, and the body form a single unit construction.

* * * * *